United States Patent
Thai et al.

(10) Patent No.: US 9,242,068 B2
(45) Date of Patent: Jan. 26, 2016

(54) SPIRALLY CONFORMABLE INFUSION CATHETER

(75) Inventors: Michael Thai, San Jose, CA (US);
Thomas Chien, San Jose, CA (US);
Kelvin Ning, Palo Alto, CA (US);
Robert Mcrae, San Jose, CA (US)

(73) Assignee: Covidien LP, Mansfield, MA (US)

(*) Notice: Subject to any disclaimer, the term of this patent is extended or adjusted under 35 U.S.C. 154(b) by 1683 days.

(21) Appl. No.: 12/505,191

(22) Filed: Jul. 17, 2009

(65) Prior Publication Data

US 2010/0016832 A1 Jan. 21, 2010

Related U.S. Application Data

(60) Provisional application No. 61/081,681, filed on Jul. 17, 2008.

(51) Int. Cl.
*A61M 25/00* (2006.01)
*A61M 25/01* (2006.01)

(52) U.S. Cl.
CPC ......... *A61M 25/0021* (2013.01); *A61M 25/003* (2013.01); *A61M 25/007* (2013.01); *A61M 25/0102* (2013.01); *A61M 2025/0024* (2013.01); *A61M 2025/0037* (2013.01); *A61M 2025/0057* (2013.01); *A61M 2025/0063* (2013.01)

(58) Field of Classification Search
CPC .......... A61M 25/0021; A61M 25/003; A61M 25/007; A61M 25/0102; A61M 2025/0024; A61M 2025/0037; A61M 2025/0057; A61M 2025/0063

USPC ............... 604/107, 108, 164.01, 164.03, 604/508–510, 523, 524, 528–532
See application file for complete search history.

(56) References Cited

U.S. PATENT DOCUMENTS

| | | | |
|---|---|---|---|
| 4,706,671 A | 11/1987 | Weinrib | |
| 4,848,342 A | 7/1989 | Kaltenbach | |
| 5,131,407 A | 7/1992 | Ischinger et al. | |
| 5,184,627 A | 2/1993 | de Toledo | |
| 5,246,445 A | 9/1993 | Yachia et al. | |
| 5,391,146 A | 2/1995 | That et al. | |
| 5,460,614 A | 10/1995 | Castaneda | |
| 5,730,741 A | 3/1998 | Horzewski et al. | |
| 5,766,201 A | 6/1998 | Ravenscroft et al. | |
| 5,827,304 A | 10/1998 | Hart | |
| 5,836,947 A | 11/1998 | Fleischman et al. | |
| 5,843,103 A | 12/1998 | Wulfman | |
| 5,873,865 A | 2/1999 | Horzewski et al. | |
| 6,048,356 A | 4/2000 | Ravenscroft et al. | |
| 6,053,900 A | 4/2000 | Brown et al. | |
| 6,063,069 A * | 5/2000 | Cragg et al. | 604/508 |
| 6,254,571 B1 | 7/2001 | Hart | |

(Continued)

*Primary Examiner* — Kami A Bosworth

(57) ABSTRACT

An infusion catheter includes a catheter body having a proximal end, a distal end, and two or more lumens extending therethrough. The infusion catheter also includes an infusion tube having a proximal end, a distal end, and one or more ports disposed therethrough. The first lumen of the catheter body is in fluid communication with the lumen of the infusion tube. A central member has a distal end connected to the distal end of the infusion tube, a proximal end, and a proximal portion slidably received in the second lumen of the catheter body. The infusion tube is disposed relative to the central member such that axial advancement of the central member relative to the catheter body radially collapses the infusion tube over the central member and axial retraction of the central member relative to the catheter body radially expands the infusion tube about the central member.

18 Claims, 7 Drawing Sheets

(56) References Cited

U.S. PATENT DOCUMENTS

| | | |
|---|---|---|
| 6,402,736 B1 | 6/2002 | Brown et al. |
| 6,425,908 B2 | 7/2002 | Ravenscroft et al. |
| 6,454,775 B1 | 9/2002 | Demarais et al. |
| 6,542,781 B1 | 4/2003 | Koblish et al. |
| 6,629,987 B1 | 10/2003 | Gambale et al. |
| 6,660,014 B2 | 12/2003 | Demarais et al. |
| 6,711,444 B2 | 3/2004 | Koblish |
| 6,745,080 B2 | 6/2004 | Koblish |
| 6,902,540 B2 | 6/2005 | Dorros et al. |
| 6,945,977 B2 | 9/2005 | Demarais et al. |
| 7,090,695 B2 | 8/2006 | Solem et al. |
| 7,416,555 B2 | 8/2008 | Krivoruchko |
| 2002/0072706 A1 | 6/2002 | Hiblar et al. |
| 2003/0040704 A1 | 2/2003 | Dorros et al. |
| 2004/0225297 A1 | 11/2004 | Chen |
| 2004/0260239 A1 | 12/2004 | Kusleika |
| 2005/0124973 A1 | 6/2005 | Dorros et al. |
| 2005/0267323 A1 | 12/2005 | Dorros et al. |
| 2006/0085054 A1 | 4/2006 | Zikorus et al. |
| 2008/0015541 A1 | 1/2008 | Rosenbluth et al. |
| 2009/0054824 A1 | 2/2009 | Melsheimer et al. |
| 2009/0125009 A1 | 5/2009 | Zikorus et al. |

* cited by examiner

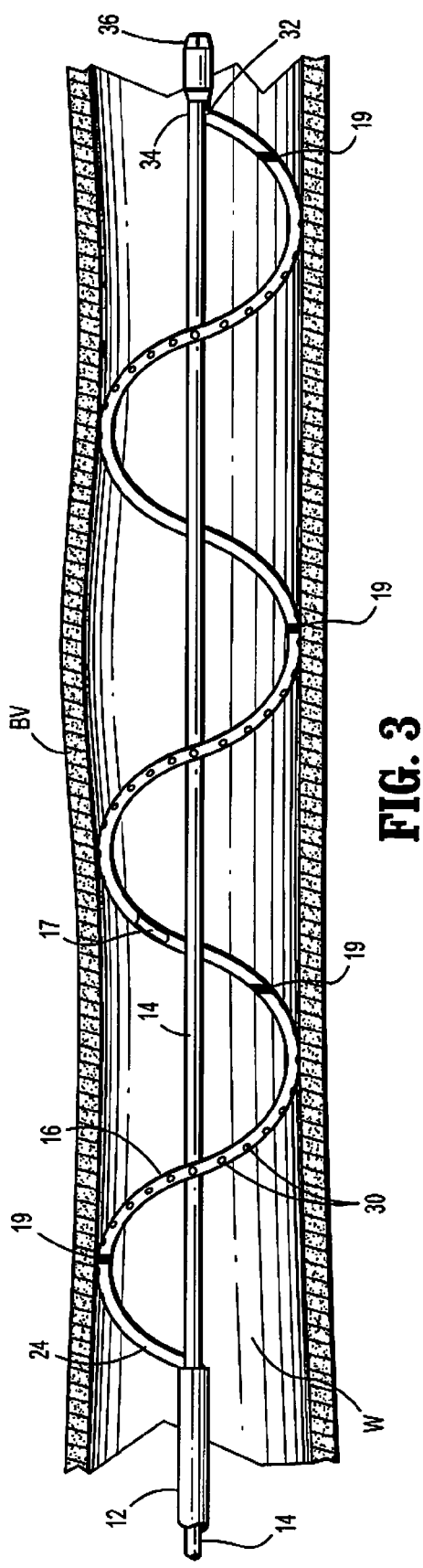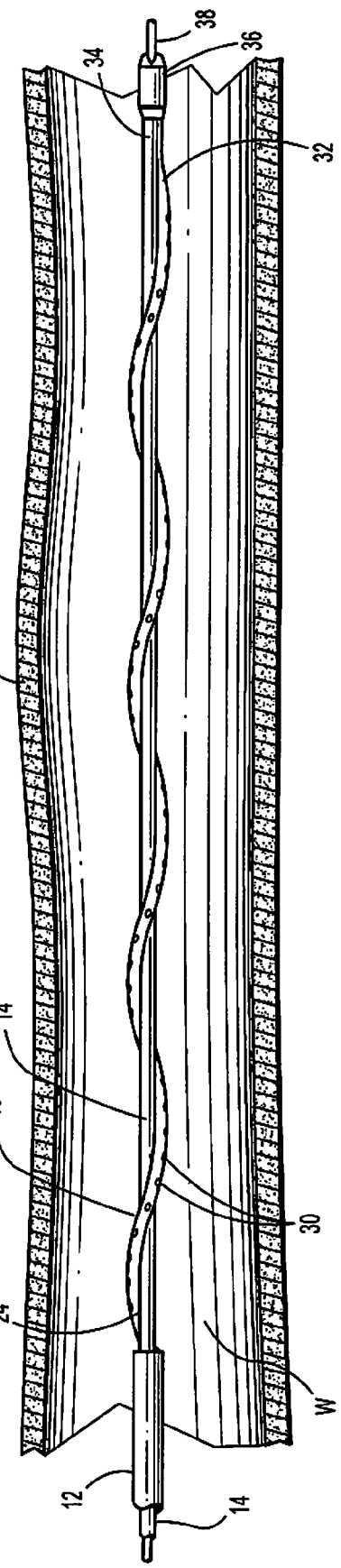
FIG. 3
FIG. 3A

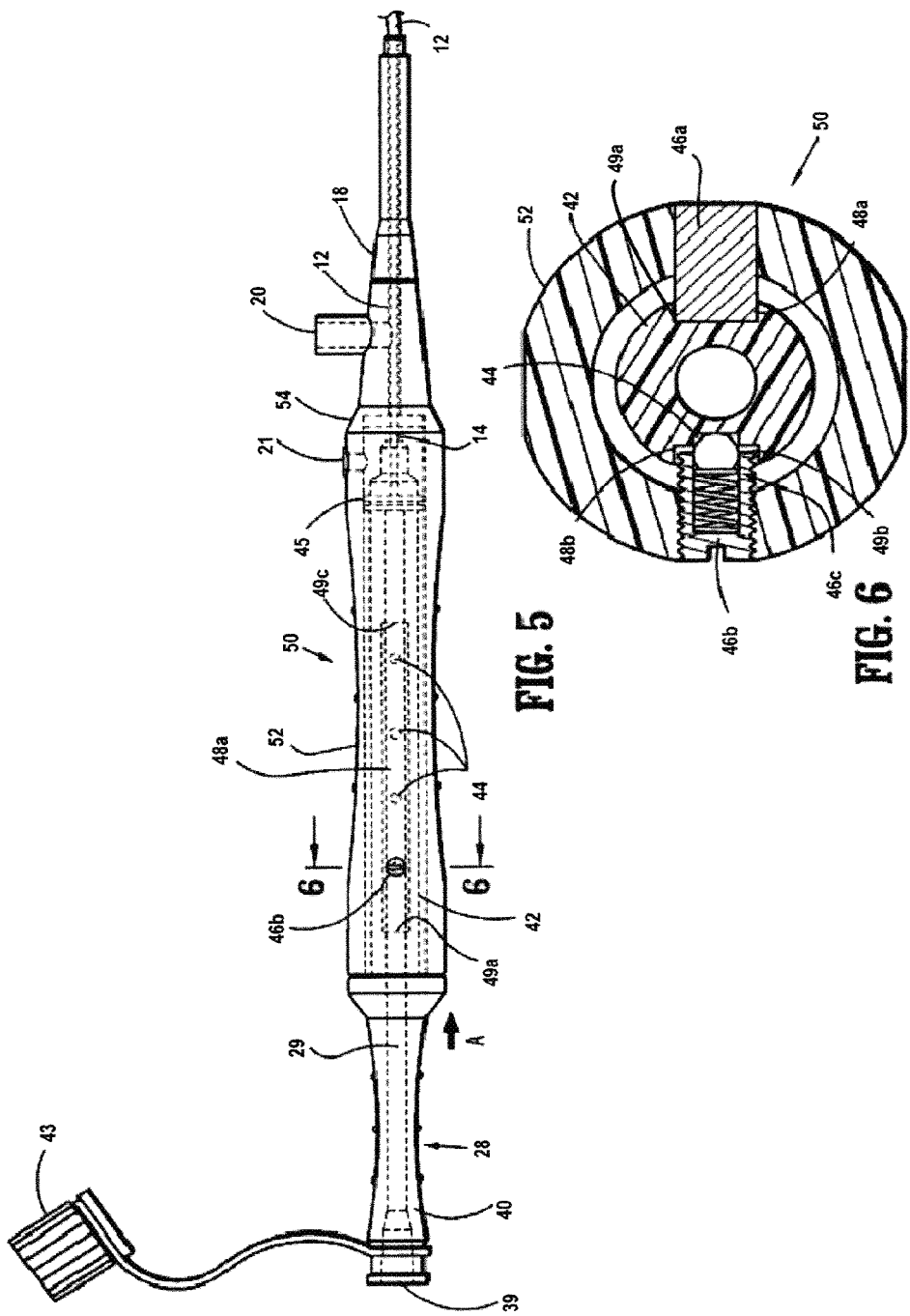

SPIRALLY CONFORMABLE INFUSION CATHETER

CROSS-REFERENCE TO RELATED APPLICATION

The present application claims the benefit of and priority to U.S. Provisional Patent Application Ser. No. 61/081,681 filed Jul. 17, 2008, which is incorporated herein by reference in its entirety.

BACKGROUND

1. Technical Field

The present disclosure relates generally to medical devices and methods. More particularly, the present disclosure relates to an infusion catheter and methods for its use in delivering substances to vasculature.

2. Description of the Related Art

Catheters are used for delivering drugs through vasculature and other body lumens for a wide variety of purposes. It is often desirable to deliver thrombolytic and other substances to the peripheral vasculature, in particular the peripheral venous vasculature, in order to lyse and help remove clots in patients suffering from deep vein thrombosis (DVT) and other conditions. A number of catheters have been proposed for this purpose. For example, the catheter illustrated in U.S. Pat. No. 5,554,114 includes a pre-shaped spiral coil at its distal end, where the coil can be reduced to a smaller diameter by axially advancing a core wire to facilitate introduction into the vasculature. Although the benefits of such a pre-shaped coil are clearly evident, since the maximum diameter of the coil is fixed, the coil may be too small to treat relatively large blood vessels and may have difficulty in adequately conforming to and delivering thrombolytic and other agents throughout the length of the vessel to be treated especially in vessels of varying diameters. Thus, it would be desirable to provide alternative and improved catheters and methods for delivering thrombolytic agents to the venous and other vasculature.

SUMMARY

An infusion catheter useful for delivering drugs to the peripheral venous and other vasculature comprises a catheter body, an infusion tube, and a central member. The catheter body has a proximal end, a distal end, and at least a first lumen and a second lumen therethrough. The infusion tube has a proximal end, a distal end, and at least one lumen therethrough, where the proximal end of the infusion tube is connected to the distal end of the catheter body. The infusion tube and catheter body are connected and aligned so that the first lumen of the catheter body is in fluid communication with the lumen of the infusion tube so that substances delivered through the first lumen of the catheter body will flow into and through the lumen of the infusion tube. The infusion tube, in turn, is adapted to deliver liquid agents through its wall, typically having a plurality of perfusion ports formed therethrough. Alternatively, the infusion tube could be porous, perforate, slitted, slotted, or otherwise provided with flow passages adapted to release therapeutic, diagnostic, and other substances through its wall into the blood vessel or other body lumen being treated.

The central member has a distal end and a proximal end, where the distal end of the central member is connected to the distal end of the infusion tube. The proximal portion of the central member is slidably received in the second lumen of the catheter body. In this way, the central member may be axially advanced and retracted in order to lengthen and foreshorten the infusion tube, respectively. The infusion tube may be wrapped around the central member one or more times so that, when the central member is axially extended, the infusion tube will be closely positioned about the outer surface of the central member to facilitate insertion of the infusion catheter into a body lumen. Conversely, when the central member is axially retracted in the proximal direction, the infusion tube will expand radially outwardly. Advantageously, it has been found that the infusion tube will assume a generally helical or spiral configuration against the inner wall of the blood vessel or other body lumen in which it has been radially expanded. The helical or spiral configuration helps distribute the drug being delivered to the luminal wall being treated more uniformly in the radial direction.

In embodiments of the present disclosure, the infusion tube has a generally straight or linear shape or configuration. That is, when left in neither tension nor compression, the infusion tube will assume a generally straight configuration. In embodiments, a straight stiffening wire is provided within the lumen of the infusion tube in order to provide column strength. Usually, the infusion tube will have a polymeric body with a certain degree of stiffness, such as a nylon polymer having a stiffness or hardness in the range from about 50 kpsi to about 800 kpsi. Providing the stiffening wire increases the column strength of the infusion tube. The real advantage, however, is that when the infusion tube is foreshortened, the stiffening wire helps provide a greater hoop strength as the infusion tube assumes its spiral or helical configuration about the central member. Typically, the stiffening wire is a stainless steel wire having a diameter in the range from about 0.08 mm to about 0.7 mm. The stiffening wire is attached at its distal end to the infusion tube at or near the distal end of the infusion tube. The stiffening wire extends through the entire length of the infusion tube and into the first lumen within the catheter body. Still more usually, a proximal end of the stiffening wire will not be attached to the catheter body, i.e. it will be free so that it can move distally and proximally as the catheter body and infusion wire are bent when advanced through the vasculature or other body lumen.

In embodiments for the treatment of the peripheral vasculature, the infusion tube typically has a length in the range from about 1 cm to about 100 cm, and a width, typically an outer diameter, in the range from about 0.3 mm to about 2.8 mm. The catheter body, in turn, has a length in the range from about 5 cm to about 150 cm, and a width, typically an outer diameter, in the range from about 0.66 mm to about 4 mm, and the central member has a length in the range from about 10 cm to about 175 cm, and a width, typically a diameter, in the range from about 0.4 mm to about 3.7 mm. In still other embodiments, the infusion tube will have ports for releasing the substance, and the ports will be formed along its length. The ports may be spaced apart by distances in the range from about 2.5 mm to about 50 mm and may have width or diameter dimensions in the range from about 0.01 mm to about 0.25 mm. In still further specific embodiments, the ports may have variable spacing or porosity along the length of the infusion tube, in order to provide or improve uniform distribution.

Thrombolytic and other substances may be delivered to body lumens, particularly the peripheral venous vasculature, using the catheter as described above. For example, the central member may be advanced to draw the infusion tube to a target location within the body lumen, typically a location which is at least partially occluded with thrombus. After being positioned within the treatment region, the central member is drawn proximally to foreshorten the infusion tube and radially deploy the infusion tube outwardly so that it expands toward a wall portion of the body lumen in a helical or spiral geometry, including the regions of thrombus which may be formed along the wall surface. The thrombolytic or other substance may then be introduced into the lumen of the infusion tube so that the substance infuses outwardly through the ports or other release structures toward the wall of the body lumen, typically infusing into the thrombus in order to help break up and dissolve the thrombus or other occlusive materials.

As described above in connection with the apparatus of the present disclosure, the infusion tube will generally have a straight configuration, i.e. will have a certain elasticity which assumes a straight configuration when neither tension nor compression are being applied. The infusion tube may be helically wrapped, coiled or spiraled around the central member to provide for a more compact profile when the central member is in an advanced position. Alternatively, the infusion tube may be substantially axially aligned with the central member when the central member is in an advanced position. The infusion tube of the present disclosure is capable of conforming to regions of widely varying diameter within the body lumen to assure good contact and/or efficient delivery of the thrombolytic and other substances into the lumen. The structure of the present disclosure is also particularly useful for treating very long regions within a body lumen, typically regions extending from about 1 cm to about 100 cm within a peripheral vein.

BRIEF DESCRIPTION OF THE DRAWINGS

Various embodiments of the presently disclosed catheter are described herein with references to the accompanying drawings, wherein:

FIG. 1A is a perspective detail view of the portion of FIG. 1 located in the oval labeled 1A-1A;

FIG. 3 illustrates the catheter of FIG. 1 within a body lumen with the central member retracted and the infusion lumen radially expanded;

FIG. 3A illustrates the catheter of FIG. 1 within a body lumen with the central member advanced and the infusion lumen in a collapsed configuration;

FIG. 4 is a cross-sectional view taken along line 4-4 of FIG. 1;

FIG. 5 is a side cross-sectional view of a portion of the catheter of FIG. 1 according to an embodiment of the present disclosure;

FIG. 6 is a cross-sectional view taken along line 6-6 of FIG. 5;

DETAILED DESCRIPTION

Figure 1:
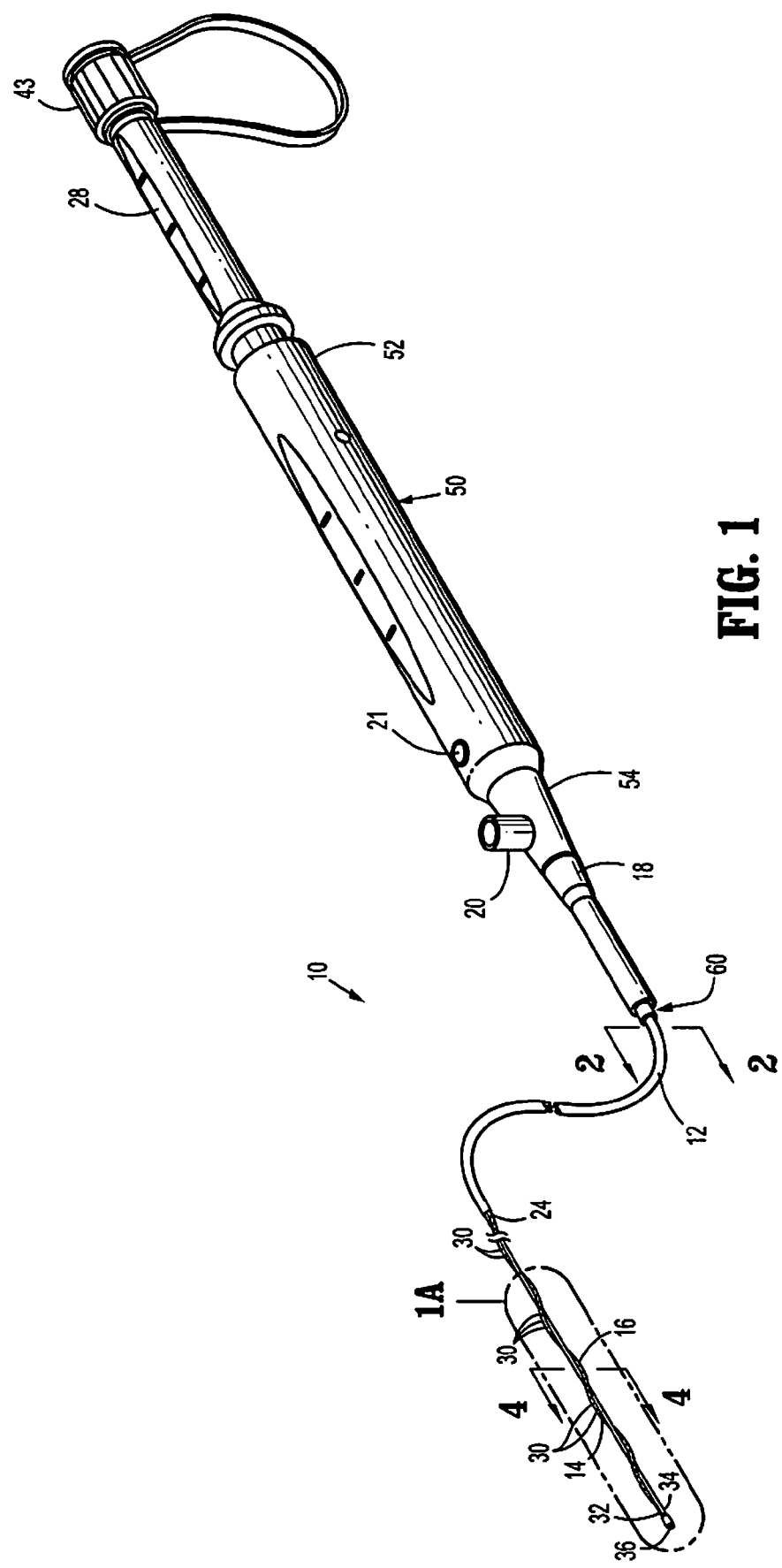
FIG. 1 is a perspective view of a substance delivery catheter constructed in accordance with an embodiment of the present disclosure.

Embodiments of the presently disclosed catheter assembly will now be described in detail with reference to the drawings wherein like reference numerals identify similar or identical elements in each of the several views. In the discussion that follows, the term "proximal" or "trailing" will refer to the portion of a structure that is closer to a user, while the term "distal" or "leading" will refer to the portion of the structure that is farther from the user. In addition, the term spiral as used in association with the infusion tube and the central member means that the infusion tube extends along and at least partially around the central member in a helical, coiled or like configuration.

Referring initially to FIGS. 1-4, a catheter assembly 10 constructed in accordance with the principles of the present disclosure includes a handle housing 50, a movable handle 28, a catheter body 12, a central member 14, and an infusion tube 16. Catheter body 12 extends at least partially into a distal end 54 of handle housing 50 and includes a hub 18 at its proximal end that operates to reinforce the coupling of catheter body 12 into the distal end 54 of handle housing 50. Hub 18 may be, for example, flexible shrink wrap tubing encapsulating at least a portion of the distal end 54 of handle housing 50 and at least a portion of a proximal end of catheter body 12. Handle housing 50 includes a first connector 20 at or near its distal end 54 for attaching to a fluid source such as a source of a thrombolytic agent to be delivered through the catheter body 12 and a second connector 21 at or near its distal end 54 for attaching to saline or other liquid for flushing the catheter body 12.

Figure 2:
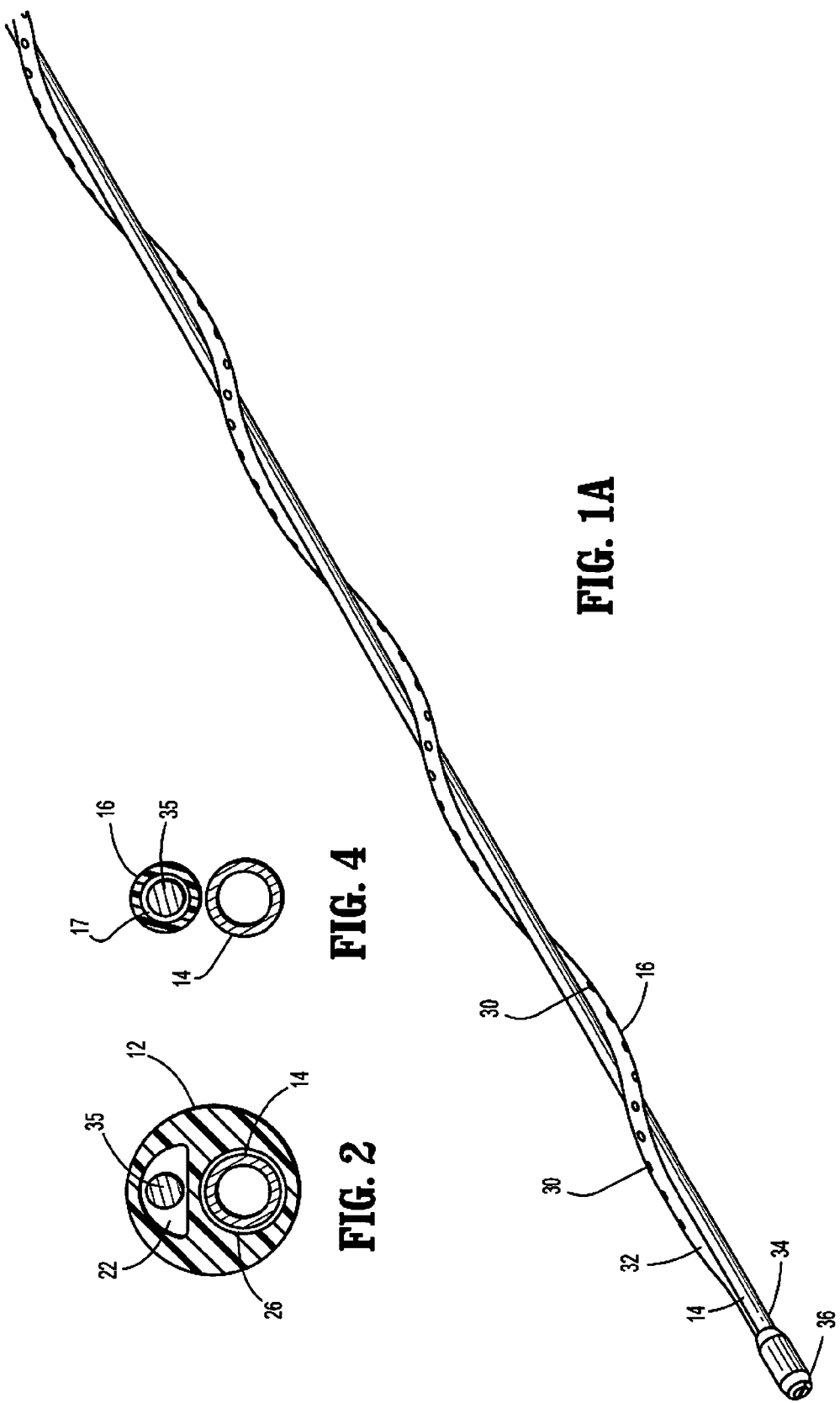
FIG. 2 is a cross-sectional view taken along line 2-2 of FIG. 1.

As shown in the cross section of FIG. 2, the catheter body 12 defines a first lumen 22 that receives the thrombolytic or other agent through the port 20 and delivers it to a proximal end 24 of the infusion tube 16. The proximal end 24 of infusion tube 16 may be shrink wrapped (not explicitly shown) and heated to bond the proximal end 24 of infusion tube 16 to first lumen 22 of catheter body 12 at a mid-joint 60 (FIG. 1) via shrink wrap tubing (not explicitly shown). Catheter body 12 includes a second lumen 26 which slidably receives the central member 14 which is typically a polymeric tube or the like operably coupled to the handle 28 at its proximal end. Using the handle 28, a physician can axially advance (see FIG. 5) and proximally retract (see FIG. 7) the central member 14 in order to control deployment of the infusion tube 16, as will be described in more detail with reference to FIGS. 3, 5, and 7.

The infusion tube 16 is straight in its "free" configuration, i.e. where no tension or compression is being applied to the infusion tube 16. In certain embodiments, the polymeric material (e.g., nylon-12) from which the infusion tube 16 is made may possess sufficient stiffness and elasticity without reinforcement to perform as described herein. Alternatively, as illustrated in FIG. 4, a stiffening member or wire 35 that extends through at least a portion of the lumen of the infusion tube 16 may be provided to provide added rigidity to infusion tube 16. In this scenario, a distal end of the stiffening member or wire 35 is attached at or near its distal end to the distal end of the infusion tube 16 and attached at its proximal end to the catheter body 12 within the infusion lumen 22, as best seen in FIG. 2. In other embodiments, however, a proximal end of the stiffening wire 35 is unattached at its proximal end so that the proximal portion of the stiffening wire may move freely within the lumen 22 of the catheter body as the catheter itself is advanced through a body lumen.

As best seen in FIGS. 1 and 3, a one-way valve 36 (e.g., a duckbill valve) may be provided at or near the distal end 34 of the central member 14 in order to prevent back-bleed, i.e., blood flow into central member 14. One-way valve 36 may be, for example, shrink wrapped or heat-sealed to central member 14 to reduce the cross-sectional profile of catheter assembly 10 and enable catheter assembly 10 to be introduced into a blood vessel or other body lumen. One way valve 36 also facilitates the introduction of a guide wire 38 (see FIG. 3A) or a medical fluid into vasculature via central member 14.

The infusion tube 16 defines a lumen 17 (see FIG. 3) along its length and further includes a plurality of release ports 30 which serve to release fluid from the lumen 17 into a blood vessel BV or other luminal wall.

Relative to infusion tube 16, the material from which the central member 14 is made is more rigid or stiff. For example, central member 14 may be made from a polymer such as a polyimide or polyetheretherketone ("PEEK"). A distal end 32 of the infusion tube 16 is attached near distal end 34 of the central member 14 so that axial advancement of the central member 14 operates to lengthen or elongate the infusion tube 16, as shown in FIG. 1, in order to reduce the cross-sectional profile of the infusion tube 16 to enable the infusion tube 16 to be introduced into a blood vessel or other body lumen.

Conversely, proximal retraction of the central member 14, as shown in FIG. 3, radially expands the infusion tube 16 so that it moves outwardly toward the inner wall W of the blood vessel BV or other body lumen. The infusion tube 16 may be spirally or helically wrapped around the central member 14 in its deployment configuration, as shown in FIGS. 1 and 3A.

Figure 3B:
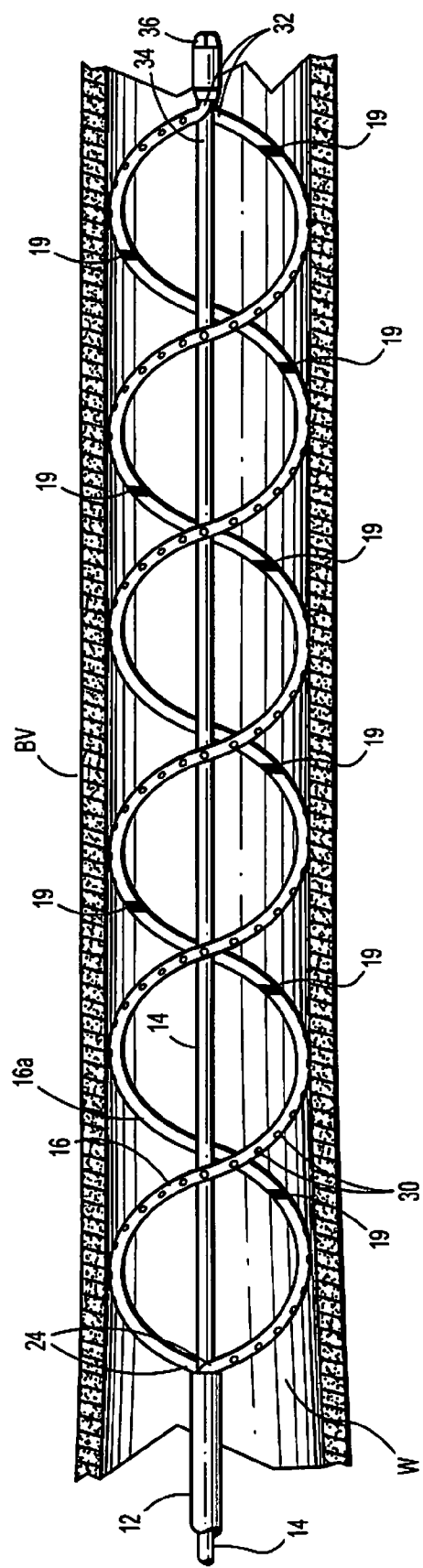
FIG. 3B illustrates an alternative embodiment of the presently disclosed catheter within a body lumen with a pair of infusion lumens radially expanded.

As shown in FIGS. 1, 3 and 3B, one or more radio-opaque markers or bands 19 may be disposed on the catheter body, central member, and/or infusion tube 16 and/or 16a to allow for clear visualization of the treatment region using fluoroscopic imaging. In addition, to promote visualization of the treatment region, the infusion tube 16 may be comprised of a radiopaque filler such as barium sulfate, for example.

Referring now to FIGS. 5-8, central member 14 extends proximally from catheter body 12 at least partially within handle housing 50 and is operably coupled to a distal end 42 of movable handle 28. Distal end 42 of movable handle 28 is configured to axially reciprocate within proximal end 52 of handle housing 50 to control movement of central member 14. More specifically and as shown in FIG. 5, as movable handle 28 is axially advanced, as depicted by directional arrow "A", tension in central member 14 is substantially reduced or eliminated such that infusion tube 16 is lengthened or elongated, as shown in FIG. 1. As best shown in the cross-section of FIG. 8, distal end 42 of movable handle 28 includes an annular bushing 45 having an outer surface for sliding engagement with an inner surface of handle housing 50. Annular bushing 45 operates to coaxially stabilize movable handle 28 centrally within handle housing 50 during axial retraction and advancement of handle 28. In addition, annular busing 45 acts as a seal to allow pressurized flushing of the annular space between central member 14 and catheter body 12 through second connector 21.

Figure 7:
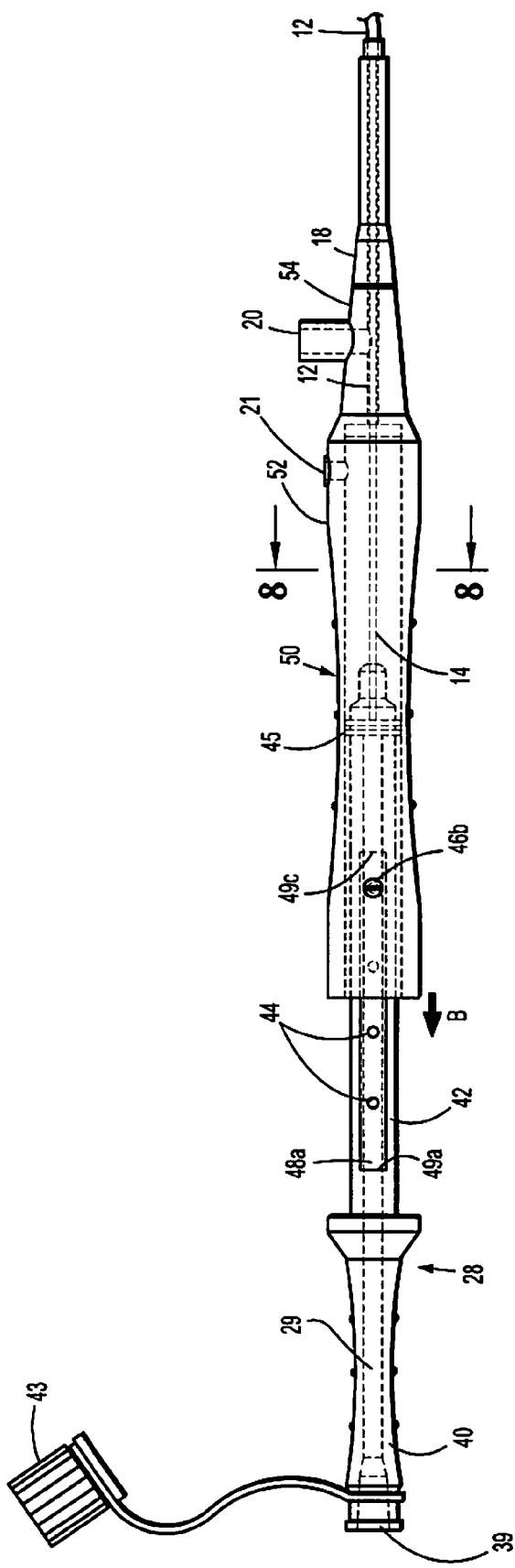
FIG. 7 is a side cross-sectional view of a portion of the catheter of FIG. 1 according to an embodiment of the present disclosure.
Figure 8:
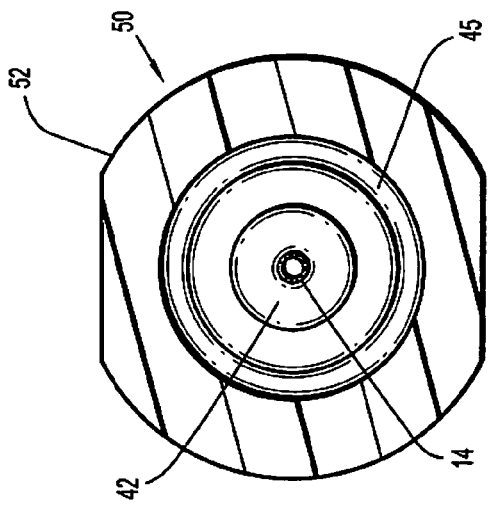
FIG. 8 is a cross-sectional view taken along the line 8-8 of FIG. 7.
Figure 9:
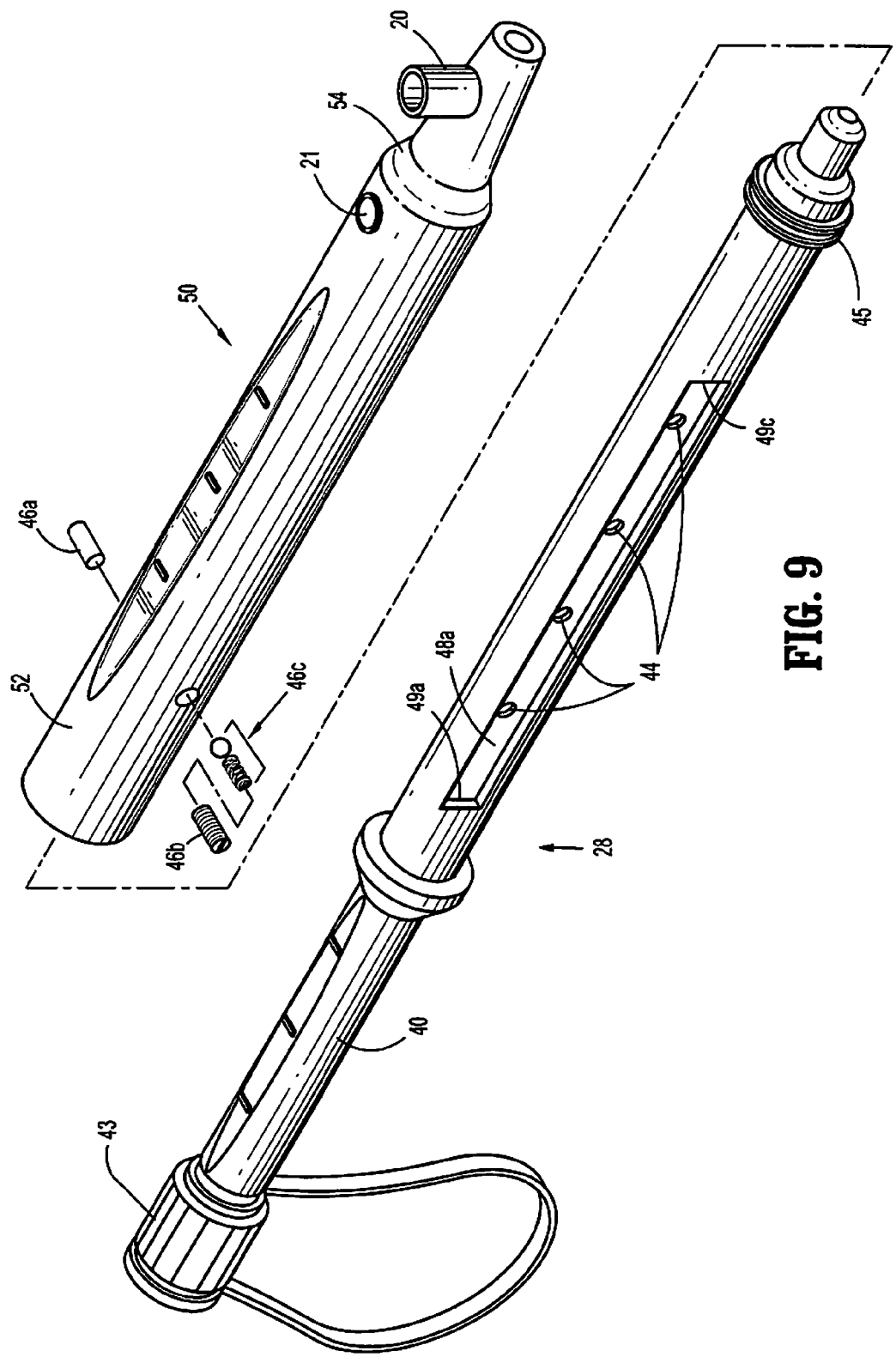
FIG. 9 is a side perspective view of a portion of the catheter shown in FIG. 1, with parts separated.

As shown in FIG. 7, as movable handle 28 is axially retracted within handle housing 50, as depicted by directional arrow "B", infusion tube 16 is compressed by central member 14 such that infusion tube 16 shortens and radially expands toward the inner wall W of the blood vessel BV or other body lumen.

As best shown in the cross-section of FIG. 6, movable handle 28 includes a pair of longitudinal recesses 48a, 48b disposed at least partially along opposing sides of the distal end 42 of movable handle 28. A pair of pins 46a, 46b are disposed through opposing sides of handle housing 50. Pins 46a and 46b are configured to be received within longitudinal recesses 48a, 48b, respectively, of a movable handle 28. A plurality of indents 44 are incrementally formed within longitudinal recesses 48a such that upon axial translation of handle 28, pin 46b is configured to be brought into and out of registration with indents 44. Indents 44 may be axially spaced apart in a substantially uniform manner such that proximal retraction and/or axial advancement of movable handle 28 may be incrementally controlled to provide controlled radial expansion and contraction of infusion tube 16 within a blood vessel or other body lumen. In this way, infusion tube 16 may be manipulated in a controlled manner to conform to blood vessels or body lumens of various sizes. In one embodiment, pin 46b is configured to receive a spring-loaded ball or detent 46c which allows for distinct engagement with indents 44. Alternatively, other known flexible or resilient engagement devices may be provided to releasably retain movable handle 28 at fixed positions in relation to handle housing 50.

One or both of pins 46a, 46b may be, for example, a dowel pin, a threaded fastener, a spring plunger, or the like, and may be adjusted (i.e., advanced into handle housing 50 or retracted from handle housing 50) as needed. In this manner, the size (e.g., circumference) of the housing and/or handle utilized may be varied without compromising interaction between pins 46a, 46b and longitudinal recesses 48a, 48b.

As can be seen in FIGS. 5 and 6, longitudinal recesses 48a, 48b include a pair of distal travel limiting stops 49a, 49b, respectively. In use, movable handle 28 may be advanced until pins 46a, 46b engage distal travel limiting stops 49a, 49b, respectively. Similarly, as can be seen in FIG. 7, longitudinal recesses 48a, 48b include a pair of proximal travel limiting stops 49c (only one is illustrated) which engage pins 46a, 46b to limit or prevent further axial retraction of movable handle 28.

As movable handle 28 is moved proximally, as illustrated by directional arrow "B" in FIG. 7, the central member 14 is retracted to cause the infusion tube 16 to radially expand into a generally spiral configuration, as shown in FIGS. 3 and 3B. Since the infusion tube 16 is not pre-shaped, however, the spiral will only form as the infusion tube engages the wall surface W of blood vessel BV, thus allowing the infusion tube to conform to a variety of different diameters and irregularities within and along the surface of the wall surface W of blood vessel. Thus, it would not necessarily be expected that the infusion tube 16 will actually achieve the uniform spiral as illustrated in FIG. 3, instead, it will more often achieve a generally helical or spiral shape which can adapt to match the topography of the wall being engaged.

As shown in FIG. 3B, catheter 10, in certain embodiments, may include a second infusion tube 16a in addition to infusion tube 16. In this scenario, infusion tube 16a operates substantially as described above with respect to infusion tube 16. Infusion tube 16a may be spirally wrapped around the central member 14 to interweave with infusion tube 16 in the deployed state (not explicitly shown) and to radially expand with infusion tube 16 into a generally spiral configuration upon retraction of movable handle 28 (FIG. 1), as shown in FIG. 3B.

After deployment as shown in FIGS. 3 and 3B, the thrombolytic or other agent may be released into the first connector 20 so that it flows through lumen 22 (FIG. 2) and into the infusion tube 16 and/or 16a for release into the blood vessel BV or other body lumen. Saline may be delivered through second connector 21 prior to any procedure to flush lumen 26.

As shown in FIGS. 1, 5, and 7, the proximal end 40 of movable handle 28 includes a female luer 39 that provides access to a lumen 29 (FIG. 5) defined through movable handle 28. Lumen 29 communicates with the lumen defined by central member 14. A male-type cap 43 may be removably fastened (e.g., via threading, snap-fit, slide-fit, etc.) into female luer 39 to prevent access or seal the proximal end of lumen 29. Upon removal of cap 43, a fluid source may be removably coupled to female luer 39 to introduce fluid such as saline into movable handle 28 and central member 14. Further, a guide wire 38 (see FIG. 3A) may be inserted through lumen 29, and into central member 14, and through one-way valve 36 to facilitate introduction of infusion lumen 16 (and/or 16a) and central member 14 into the blood vessel BV or other body lumen.

Although the specific features of the disclosure are shown in some drawings and not in others, this is for convenience only as each feature may be combined with any or all of the other features in accordance with the disclosure.

It will be understood that various modifications may be made to the embodiments of the presently disclosed delivery catheters. Therefore, the above description should not be construed as limiting, but merely as exemplifications of embodiments. Those skilled in the art will envision other modifications within the scope and spirit of the present disclosure.

What is claimed is:

1. An infusion catheter, comprising:
   a catheter body having a proximal end, a distal end, and at least a first lumen and a second lumen extending therethrough;
   an infusion tube having a proximal end, a distal end, and at least one lumen disposed therethrough adapted to deliver fluid to a body lumen, the proximal end of the infusion tube being connected to the distal end of the catheter body such that the first lumen of the catheter body is in fluid communication with the lumen of the infusion tube; and
   a central member having a distal end connected to the distal end of the infusion tube, a proximal end, and a proximal portion slidably received in the second lumen of the catheter body, the infusion tube being disposed relative to the central member such that axial advancement of the central member relative to the catheter body radially collapses the infusion tube over the central member and axial retraction of the central member relative to the catheter body radially expands the infusion tube relative to the central member.

2. An infusion catheter according to claim 1, further comprising:
   a handle housing having a distal end coupled to the proximal end of the catheter body and a proximal end configured to receive a movable handle therein, the movable handle being operably connected to the proximal end of the central member and being configured to reciprocate at least partially within the handle housing, the movable handle being movable to a retracted position to radially expand the infusion tube and to an advanced position to radially collapse the infusion tube.

3. An infusion catheter according to claim 2, wherein the movable handle includes a plurality of axially spaced detents disposed therein configured to be releasably engaged by at least one pin disposed through the handle housing such that the movable handle discretely reciprocates within the handle housing.

4. An infusion catheter according to claim 2, wherein the central member defines a central lumen configured to receive a guide wire therethrough, the guide wire configured to extend through the movable handle and the central lumen of the central member to facilitate introduction of the infusion tube and the central member into the body lumen.

5. An infusion catheter according to claim 1, wherein the infusion tube is wrapped at least partially around the central member.

6. An infusion catheter according to claim 1, wherein the infusion tube is a polymeric tube, further comprising a straight stiffening wire disposed in at least a portion of the lumen of the infusion tube.

7. An infusion catheter according to claim 6, wherein the stiffening wire is attached near a distal end thereof to the infusion tube and wherein a proximal end of the stiffening wire extends into the first lumen of the catheter body but is unattached to the catheter body.

8. An infusion catheter according to claim 1, further comprising:
   at least one radio-opaque marker disposed on at least one of the catheter body, central member and infusion tube.

9. An infusion catheter according to claim 1, further comprising:
   a radiopaque filler doped in the infusion tube.

10. An infusion catheter according to claim 1, wherein the infusion tube has a length in the range from about 1 cm to about 100 cm, and a width in the range from about 0.3 mm to about 2.8 mm.

11. An infusion catheter according to claim 1, wherein the catheter body has a length in the range from about 5 cm to about 150 cm and a width in the range from about 0.66 mm to about 4 mm.

12. An infusion catheter according to claim 1, wherein the central member has a length in the range from about 10 cm to about 175 cm and a width in the range from about 0.4 mm to about 3.7 mm.

13. An infusion catheter according to claim 1, wherein the infusion tube has ports formed along its length, said ports being spaced apart by distances in the range from about 2.5 mm to about 50 mm and having a width in the range from about 0.01 mm to about 0.25 mm.

14. An infusion catheter according to claim 1, wherein the ports have variable spacing along the length of the infusion tube.

15. A method for delivering a fluid to a body lumen, said method comprising:
   providing an infusion catheter having a catheter body with a distal end and at least a first lumen extending therethrough, an infusion tube having a proximal end, and a central member, the proximal end of the infusion tube being connected to the distal end of the catheter body such that the first lumen of the catheter body is in fluid communication with a lumen of the infusion tube, a distal end of the infusion tube being connected to a distal end of the central member;
   advancing the infusion tube to a target location within a body lumen;
   drawing proximally on the central member to foreshorten the infusion tube and cause the infusion tube to deploy radially outwardly relative to the central member and assume a spiral configuration within the body lumen; and
   introducing a fluid into the lumen of the infusion tube so that the fluid infuses through at least a portion of a wall of the infusion tube into the body lumen.

16. A method according to claim 15, wherein the infusion tube is wrapped around the central member so that the infusion tube deploys spirally toward a wall portion of the body lumen when the central member is drawn proximally.

17. A method according to claim 15, wherein the body lumen is a vein.

18. A method according to claim 15, wherein the infusion tube extends for about 1 cm to about 100 cm along a body lumen.

* * * * *